United States Patent
Wang (10) Patent No.: US 10,413,179 B2
(45) Date of Patent: Sep. 17, 2019

(54) INFRARED FUNDUS IMAGING SYSTEM

(71) Applicant: Welch Allyn, Inc., Skaneateles Falls, NY (US)

(72) Inventor: Ynjiun Paul Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 144 days.

(21) Appl. No.: 15/398,145

(22) Filed: Jan. 4, 2017

(65) Prior Publication Data

US 2017/0196452 A1 Jul. 13, 2017

Related U.S. Application Data

(60) Provisional application No. 62/275,880, filed on Jan. 7, 2016.

(51) Int. Cl.
| | | |
|---|---|---|
| *A61B 3/12* | (2006.01) | |
| *A61B 3/00* | (2006.01) | |
| *A61B 3/113* | (2006.01) | |
| *A61B 3/14* | (2006.01) | |
| *G02B 5/20* | (2006.01) | |

(52) U.S. Cl.
CPC ............. *A61B 3/12* (2013.01); *A61B 3/0025* (2013.01); *A61B 3/113* (2013.01); *A61B 3/14* (2013.01); *G02B 5/208* (2013.01)

(58) Field of Classification Search
CPC .................................................. A61B 3/12–14
USPC ........................................................ 351/206
See application file for complete search history.

(56) References Cited

U.S. PATENT DOCUMENTS

| | | | |
|---|---|---|---|
| 5,048,946 A | * | 9/1991 | Sklar ..................... A61B 3/1225 351/206 |
| 5,557,350 A | | 9/1996 | Yano |
| 5,599,276 A | | 2/1997 | Hauptli et al. |
| 5,703,621 A | | 12/1997 | Martin et al. |

(Continued)

FOREIGN PATENT DOCUMENTS

| | | |
|---|---|---|
| CN | 102324014 A | 1/2012 |
| CN | 102626304 A | 8/2012 |

(Continued)

OTHER PUBLICATIONS

Dilating Eye Drops, AAPOS, http://web.archive.org/web/2012020409024/http://www.aapos.org/terms/conditions/43, Dilating Eye Drops, 2pgs, Dec. 17, 2015.

(Continued)

*Primary Examiner* — Nicholas R. Pasko
(74) *Attorney, Agent, or Firm* — Merchant & Gould P.C.

(57) ABSTRACT

A fundus imaging system is used to generate fundus images when a patient has not received mydriatic pharmaceuticals. The fundus imaging system includes a processor and memory, an infrared light source, and an image sensor array. The infrared light source illuminates the patient's fundus using only infrared light. The fundus imaging system uses one or more different near-infrared wavelengths to illuminate the patient's fundus, and the fundus imaging system captures images during infrared light illumination. Then the fundus imaging system generates a color image of the patient's eye fundus based on generated lightness maps of the infrared-illuminated images.

16 Claims, 6 Drawing Sheets

(56) References Cited

U.S. PATENT DOCUMENTS

| | | | |
|---|---|---|---|
| 5,713,047 A | 1/1998 | Kohayakawa | |
| 5,776,060 A * | 7/1998 | Smith | A61B 5/14555 |
| | | | 128/920 |
| 5,784,148 A | 7/1998 | Heacock | |
| 5,943,116 A | 8/1999 | Zeimer | |
| 6,000,799 A | 12/1999 | Van de Velde | |
| 6,011,585 A | 1/2000 | Anderson | |
| 6,120,461 A | 9/2000 | Smyth | |
| 6,296,358 B1 | 10/2001 | Cornsweet et al. | |
| 6,301,440 B1 | 10/2001 | Bolle et al. | |
| 6,307,526 B1 | 10/2001 | Mann | |
| 6,309,070 B1 | 10/2001 | Svetliza et al. | |
| 6,325,511 B1 | 12/2001 | Mizouchi | |
| 6,350,031 B1 | 3/2002 | Lashkari | |
| 6,556,853 B1 | 4/2003 | Cabib et al. | |
| 6,666,857 B2 | 12/2003 | Smith | |
| 7,134,754 B2 * | 11/2006 | Kerr | A61B 3/1241 |
| | | | 351/206 |
| 7,264,355 B2 | 9/2007 | Rathjen | |
| 7,284,859 B2 | 10/2007 | Ferguson | |
| 7,311,400 B2 | 12/2007 | Wakil et al. | |
| 7,364,297 B2 | 4/2008 | Goldfain et al. | |
| 7,380,938 B2 | 6/2008 | Chmielewski, Jr. et al. | |
| 7,387,384 B2 | 6/2008 | Heine et al. | |
| 7,404,640 B2 | 7/2008 | Ferguson et al. | |
| 7,470,024 B2 | 12/2008 | Chinaglia et al. | |
| 7,488,294 B2 | 2/2009 | Torch | |
| 7,502,639 B2 * | 3/2009 | Kerr | A61B 3/1015 |
| | | | 600/318 |
| 7,568,628 B2 | 8/2009 | Wang et al. | |
| 7,611,060 B2 | 11/2009 | Wang et al. | |
| 7,621,636 B2 | 11/2009 | Su et al. | |
| 7,784,940 B2 | 8/2010 | Goldfain et al. | |
| 7,809,160 B2 | 10/2010 | Vertegaal et al. | |
| 7,871,164 B2 | 1/2011 | Luther et al. | |
| 7,926,945 B2 | 4/2011 | Dick et al. | |
| 7,963,653 B1 | 6/2011 | Ellman | |
| 7,976,162 B2 | 7/2011 | Flitcroft | |
| 8,109,634 B2 | 2/2012 | Gil | |
| 8,109,635 B2 * | 2/2012 | Allon | A61B 3/12 |
| | | | 351/221 |
| 8,347,106 B2 | 1/2013 | Tsuria et al. | |
| 8,366,270 B2 | 2/2013 | Pujol Ramo et al. | |
| 8,388,523 B2 | 3/2013 | Vivenzio et al. | |
| 8,444,269 B1 | 5/2013 | Ellman | |
| 8,488,895 B2 | 7/2013 | Muller et al. | |
| 8,534,837 B2 | 9/2013 | Sayeram et al. | |
| 8,577,644 B1 | 11/2013 | Ksondzyk et al. | |
| 8,585,203 B2 | 11/2013 | Aikawa et al. | |
| 8,620,048 B2 | 12/2013 | Nakano et al. | |
| 8,649,008 B2 | 2/2014 | Kashani et al. | |
| 8,696,122 B2 | 4/2014 | Hammer et al. | |
| 8,714,743 B2 | 5/2014 | Verdooner | |
| 8,879,813 B1 | 11/2014 | Solanki et al. | |
| 9,211,064 B2 | 12/2015 | Wang | |
| 9,237,847 B2 | 1/2016 | Wang et al. | |
| 9,498,126 B2 | 11/2016 | Wang | |
| 9,757,031 B2 | 9/2017 | Wang et al. | |
| 9,918,629 B2 | 3/2018 | Wang | |
| 10,136,804 B2 | 11/2018 | Wang et al. | |
| 10,154,782 B2 | 12/2018 | Farchione et al. | |
| 10,159,409 B2 | 12/2018 | Wang et al. | |
| 2002/0101568 A1 | 8/2002 | Eberl et al. | |
| 2003/0009155 A1 | 1/2003 | Pawlowski et al. | |
| 2003/0071970 A1 | 4/2003 | Donnerhacke et al. | |
| 2003/0163031 A1 | 8/2003 | Madden et al. | |
| 2003/0208125 A1 | 11/2003 | Watkins | |
| 2004/0258285 A1 | 12/2004 | Hansen et al. | |
| 2005/0012899 A1 | 1/2005 | Ferguson | |
| 2005/0043588 A1 | 2/2005 | Tsai | |
| 2005/0110949 A1 | 5/2005 | Goldfain et al. | |
| 2005/0254008 A1 | 11/2005 | Ferguson et al. | |
| 2006/0113386 A1 | 6/2006 | Olmstead | |
| 2006/0119858 A1 | 6/2006 | Knighton et al. | |
| 2006/0147095 A1 | 7/2006 | Usher et al. | |
| 2006/0202036 A1 | 9/2006 | Wang et al. | |
| 2006/0202038 A1 | 9/2006 | Wang et al. | |
| 2006/0268231 A1 | 11/2006 | Gil et al. | |
| 2007/0030450 A1 | 2/2007 | Liang et al. | |
| 2007/0174152 A1 | 7/2007 | Bjornberg et al. | |
| 2007/0188706 A1 | 8/2007 | Pearson et al. | |
| 2008/0084538 A1 | 4/2008 | Maeda et al. | |
| 2008/0165322 A1 | 7/2008 | Su et al. | |
| 2008/0231803 A1 | 9/2008 | Feldon et al. | |
| 2008/0316426 A1 | 12/2008 | Shibata et al. | |
| 2009/0096885 A1 | 4/2009 | Robinson et al. | |
| 2009/0225277 A1 | 9/2009 | Gil | |
| 2009/0275929 A1 | 11/2009 | Zickler | |
| 2009/0316115 A1 | 12/2009 | Itoh et al. | |
| 2009/0323022 A1 | 12/2009 | Uchida | |
| 2009/0323023 A1 | 12/2009 | Kogawa et al. | |
| 2010/0007848 A1 | 1/2010 | Murata | |
| 2010/0007849 A1 | 1/2010 | Liesfeld et al. | |
| 2010/0014052 A1 | 1/2010 | Koschmieder et al. | |
| 2010/0085538 A1 | 4/2010 | Masaki et al. | |
| 2010/0110375 A1 | 5/2010 | Nishio et al. | |
| 2010/0149489 A1 | 6/2010 | Kikawa et al. | |
| 2010/0208961 A1 | 8/2010 | Zahniser | |
| 2010/0238402 A1 | 9/2010 | Itoh et al. | |
| 2011/0001927 A1 | 1/2011 | Kasper | |
| 2011/0028513 A1 | 2/2011 | Zhuo et al. | |
| 2011/0043756 A1 | 2/2011 | Kahn et al. | |
| 2011/0169935 A1 | 7/2011 | Henriksen | |
| 2011/0234977 A1 | 9/2011 | Verdooner | |
| 2011/0242306 A1 | 10/2011 | Bressler et al. | |
| 2011/0261184 A1 | 10/2011 | Mason et al. | |
| 2011/0299034 A1 | 12/2011 | Walsh et al. | |
| 2011/0299036 A1 | 12/2011 | Goldenholz | |
| 2012/0002167 A1 | 1/2012 | Kondoh | |
| 2012/0033227 A1 | 2/2012 | Bower et al. | |
| 2012/0044456 A1 | 2/2012 | Hayashi | |
| 2012/0050677 A1 | 3/2012 | Ohban | |
| 2012/0121158 A1 | 5/2012 | Sekine et al. | |
| 2012/0147327 A1 | 6/2012 | Shikaumi et al. | |
| 2012/0169995 A1 | 7/2012 | Mohr et al. | |
| 2012/0200690 A1 | 8/2012 | Beasley | |
| 2012/0213423 A1 | 8/2012 | Xu et al. | |
| 2012/0218301 A1 | 8/2012 | Miller | |
| 2012/0229617 A1 * | 9/2012 | Yates | A61B 3/156 |
| | | | 348/78 |
| 2012/0229764 A1 | 9/2012 | Tomatsu et al. | |
| 2012/0248196 A1 | 10/2012 | Wang | |
| 2012/0249956 A1 | 10/2012 | Narasimha-Iyer et al. | |
| 2012/0257163 A1 | 10/2012 | Dyer et al. | |
| 2012/0281874 A1 | 11/2012 | Lure | |
| 2012/0287255 A1 | 11/2012 | Ignatovich et al. | |
| 2012/0320340 A1 | 12/2012 | Coleman, III | |
| 2013/0002711 A1 | 1/2013 | Sakagawa | |
| 2013/0010260 A1 | 1/2013 | Tumlinson et al. | |
| 2013/0016320 A1 | 1/2013 | Naba | |
| 2013/0033593 A1 * | 2/2013 | Chinnock | A61B 3/14 |
| | | | 348/78 |
| 2013/0057828 A1 | 3/2013 | de Smet | |
| 2013/0063698 A1 | 3/2013 | Akiba et al. | |
| 2013/0128223 A1 | 5/2013 | Wood et al. | |
| 2013/0162950 A1 | 6/2013 | Umekawa | |
| 2013/0169934 A1 | 7/2013 | Verdooner | |
| 2013/0176533 A1 | 7/2013 | Raffle et al. | |
| 2013/0194548 A1 | 8/2013 | Francis et al. | |
| 2013/0201449 A1 | 8/2013 | Walsh et al. | |
| 2013/0208241 A1 | 8/2013 | Lawson et al. | |
| 2013/0211285 A1 | 8/2013 | Fuller et al. | |
| 2013/0215387 A1 | 8/2013 | Makihira et al. | |
| 2013/0222763 A1 | 8/2013 | Bublitz et al. | |
| 2013/0229622 A1 | 9/2013 | Murase et al. | |
| 2013/0234930 A1 | 9/2013 | Palacios Goerger | |
| 2013/0250237 A1 | 9/2013 | Ueno | |
| 2013/0250242 A1 | 9/2013 | Cheng et al. | |
| 2013/0301004 A1 * | 11/2013 | Kahn | A61B 3/12 |
| | | | 351/206 |
| 2014/0022270 A1 | 1/2014 | Rice-Jones | |
| 2014/0104573 A1 | 4/2014 | Iwanga | |
| 2014/0111773 A1 | 4/2014 | Itoh | |
| 2014/0118693 A1 | 5/2014 | Matsuoka | |

(56) References Cited

U.S. PATENT DOCUMENTS

| | | |
|---|---|---|
| 2014/0118697 A1 | 5/2014 | Tanaka et al. |
| 2014/0180081 A1 | 6/2014 | Verdooner |
| 2014/0192320 A1 | 7/2014 | Tsao |
| 2014/0198298 A1 | 7/2014 | Cheng et al. |
| 2014/0204340 A1 | 7/2014 | Verdooner |
| 2014/0204341 A1 | 7/2014 | Murase |
| 2014/0211162 A1 | 7/2014 | Matsuoka et al. |
| 2014/0267668 A1 | 9/2014 | Ignatovich et al. |
| 2014/0268046 A1 | 9/2014 | Narasimha-Iyer et al. |
| 2014/0330352 A1 | 11/2014 | Luttrull et al. |
| 2015/0002811 A1 | 1/2015 | Ota |
| 2015/0009357 A1 | 1/2015 | Seibel et al. |
| 2015/0021228 A1 | 1/2015 | Su et al. |
| 2015/0110348 A1 | 4/2015 | Solanki et al. |
| 2015/0150449 A1 | 6/2015 | Matsumoto |
| 2015/0170360 A1 | 6/2015 | Fletcher et al. |
| 2015/0178946 A1 | 6/2015 | Krishnaswamy et al. |
| 2015/0272434 A1* | 10/2015 | Satake ............. A61B 3/0058 351/206 |
| 2015/0342459 A1 | 12/2015 | Robert et al. |
| 2016/0007845 A1 | 1/2016 | Utagawa |
| 2016/0092721 A1 | 3/2016 | Kanagasingam et al. |
| 2016/0166141 A1 | 6/2016 | Kanagasingam et al. |
| 2016/0188993 A1 | 6/2016 | Beato |
| 2016/0213249 A1* | 7/2016 | Cornsweet ............. A61B 3/12 |
| 2016/0249804 A1 | 9/2016 | Wang |
| 2016/0287068 A1 | 10/2016 | Murase et al. |
| 2016/0307341 A1 | 10/2016 | Sato et al. |
| 2017/0020389 A1 | 1/2017 | Wang et al. |
| 2017/0035292 A1 | 2/2017 | Wang |
| 2017/0119241 A1 | 5/2017 | Farchione et al. |
| 2017/0161892 A1 | 6/2017 | Tellatin et al. |
| 2017/0172675 A1 | 6/2017 | Jarc et al. |
| 2017/0181625 A1 | 6/2017 | Kawakami et al. |
| 2017/0209044 A1 | 7/2017 | Ito et al. |
| 2017/0239012 A1 | 8/2017 | Wood et al. |
| 2017/0266041 A1* | 9/2017 | Kim ............. A61B 3/12 |
| 2017/0311800 A1 | 11/2017 | Wang |
| 2017/0316565 A1 | 11/2017 | Leahy et al. |
| 2017/0332903 A1 | 11/2017 | Wang et al. |
| 2018/0092530 A1 | 4/2018 | Hart et al. |
| 2018/0140188 A1 | 5/2018 | Wang |
| 2018/0249907 A1 | 9/2018 | Wang et al. |
| 2018/0263486 A1 | 9/2018 | Farchione et al. |
| 2019/0038124 A1 | 2/2019 | Wang et al. |
| 2019/0082950 A1 | 3/2019 | Farchione et al. |

FOREIGN PATENT DOCUMENTS

| | | | |
|---|---|---|---|
| CN | 102917634 A | 2/2013 | |
| CN | 205006859 U | 2/2016 | |
| CN | 105433899 A | 3/2016 | |
| CN | 205181314 U | 4/2016 | |
| EP | 2 374 404 A1 | 10/2011 | |
| EP | 2 425 763 A1 | 7/2012 | |
| GB | 2378600 A | 12/2003 | |
| JP | 2009-172157 A | 8/2009 | |
| JP | 2011-97992 A | 5/2011 | |
| JP | 2013-059551 A1 | 4/2013 | |
| WO | 2004089214 A2 | 10/2004 | |
| WO | 2006/016366 A2 | 2/2006 | |
| WO | 2008106802 A1 | 9/2008 | |
| WO | 2010080576 A1 | 7/2010 | |
| WO | 2010/115195 A1 | 10/2010 | |
| WO | 2011029064 A1 | 3/2011 | |
| WO | 2012009702 A1 | 1/2012 | |
| WO | 2012134272 A1 | 10/2012 | |
| WO | 20133041658 A1 | 3/2013 | |
| WO | 2013/082387 A1 | 6/2013 | |
| WO | 2013107464 A1 | 7/2013 | |
| WO | 2014/182769 A1 | 11/2014 | |
| WO | 2015/044366 A1 | 4/2015 | |
| WO | 2015/100294 A1 | 7/2015 | |
| WO | 2015/170947 A1 | 11/2015 | |
| WO | WO-2015170947 A1 * | 11/2015 | ............. A61B 3/12 |
| WO | WO 2015170947 A1 * | 11/2015 | ............. A61B 3/12 |

OTHER PUBLICATIONS

International Search Report and Written Opinion for Application No. PCT/US2017/012164 dated Mar. 31, 2017, 13 pages.

Spector,The Pupils, Clinical Methods: The History, Physical, and Laboratory Examinations, 3rd Edition, pp. 300-304, Chapter 58 (1990).

Grieve, et al., Multi-wavelength imaging with the adaptive optics scanning laser Ophthalmoscope, Optics Express 12230, Dec. 11, 2006, vol. 14, No. 25, 13pgs.

Anastasakis, et al., SLO-Infrared Imaging of the Macula and its Correlation with Functional Loss and Structural Changes in Patients with Stargardt Disease, May 1, 2012, 19 pgs.

EIDON—The First True Color Confocal Scanner on the Market, www.centervue.com, Jul. 27, 2015, 12pgs.

NAVILAS, Navigated Laser Therapy—A New Era in Retinal Disease Management, www.od-os.com, (c)2015, 16pgs.

Carrasco-Zevallos, O. et al., "Pupil Tracking Optical Coherence Tomography for Precise Control of Pupil Entry Position," Biomedical Optics Express; 6(9): 3405-3419, Sep. 1, 2015, 15 pages.

Moscaritolo, Michael et al., "A Machine Vision Method for Automated Alignment of Fundus Imaging Systems," Ophthalmic Surgery Lasers & Imaging; 41(6): 607-613, Sep. 29, 2010, 7 pages.

Sahin, B. et al., "Adaptive Optics With Pupil Tracking for High Resolution Retinal Imaging," Biomedical Optics Express; 3(2): 225-239, Feb. 1, 2012, 15 pages.

Hammer, Daniel X. et al., Adaptive Optics Scanning Laser Ophthalmoscope for Stabilized Retinal Imaging, Optics Express; 14(8): 3354-3367, Apr. 17, 2006, 14 pages.

Markow, Michael S. et al., "Real-Time Algorithm for Retinal Tracking," IEEE Transactions on Biomedical Engineering; 40(12): 1269-1281, Dec. 1993, 13 pages.

Sheehy, Christy K. et al., "High-speed, Image-based eye tracking with a scanning laser ophthalmoscope," Biomedical Optics Express; 3(10): 2611-2622, Oct. 1, 2012, 12 pages.

International Search Report and Written Opinion in PCT/US2016/015653, dated May 3, 2016, 11 pages.

"A Portable, Scalable Retinal Imaging System," TI Engibous Competition Report (Spring 2012), Rice University, http://www.ti.com/corp/docs/university/docs/Rice_University_mobileVision%20Final%20Report.pdf (96 pages).

Girdwain, "Goggles Differentiate Between Stroke and Vertigo," Today's Geriatric Medicine, vol. 6 No. 4 p. 8, Today's GeriatricMedicine, Oct. 1, 2013, 2 pages.

Johns Hopkins Medicine, "Small Johns Hopkins-led study finds portable device diagnoses stroke with 100 percent accuracy," www.hopkinsmedicine.org/se/util/display_mod.cfm?MODULE=/se-server/mod/modules/semod_printpage/mod_default.cfm&PageURL-/news/media/releases/is_i . . . , Mar. 5, 2013, 2 pages.

International Search Report and Written Opinion in PCT/US2015/015124 dated May 15, 2015, 10 pages.

Brown et al., "Comparison of image-assisted versus traditional fundus examination," Eye and Brain, Dovepress, Feb. 2013, vol. 5, pp. 1-8.

Muller et al., "Non-Mydriatic Confocal Retinal Imaging Using a Digital Light Projector," Ophthalmic Technologies XXIII, 2013, downloaded from: http://proceedings.spiedigitallibrary.org, 8 pages.

Paques et al., "Panretinal, High-Resolution Color Photography of the Mouse Fundus," Investigative Ophthalmology & Visual Science, Jun. 2007, vol. 48, No. 6, pp. 2769-2774.

Visucampro NM—The Non-Mydriatic Fundus Camera System from Carl Zeiss, Carl Zeiss Meditec, International, 2005, 1 page.

Mayer et al., "Wavelet denoising of multiframe optical coherence tomography data," Biomedical Optics Express, vol. 3, No. 3, pp. 572-589 (Mar. 1, 2012).

Land, Edwin H., "The Retinex Theory of Color Visison," Scientific America, Dec. 1977, vol. 237 No. 6 p. 108-128.

(56) References Cited

OTHER PUBLICATIONS

User Manual Non-Mydriatic Retinal Camera, TOPCON Corporation, Tokyo, Japan, 106 pages (2014).

* cited by examiner

INFRARED FUNDUS IMAGING SYSTEM

CROSS REFERENCE TO RELATED APPLICATION

The present application claims priority from U.S. Provisional Patent Application No. 62/275,880, filed on Jan. 7, 2016, the disclosure of which is hereby incorporated by reference in its entirety.

BACKGROUND

Medical professionals use images of a patient's eye fundus to screen for and diagnose various diseases, such as diabetic retinopathy. Cameras produce images of the fundus while the patient has been administered pharmacological pupil dilation substances, known as mydriatic fundus imaging, or without pharmacological pupil dilation, known as non-mydriatic fundus imaging. Because pupil dilation is inversely related, in part, to the amount of ambient light, non-mydriatic fundus imaging usually occurs in low lighting environments. Medical professionals can also use fundus imaging apparatus to detect or monitor other diseases, such as hypertension, glaucoma, and papilledema.

SUMMARY

Embodiments of the present disclosure are directed to a fundus imaging system. In one aspect, a non-mydriatic fundus imaging apparatus includes a processor and a memory, an infrared light source operatively coupled to the processor, and an image sensor array operatively coupled to the processor. The memory stores instructions that, when executed by the processor, cause the apparatus to illuminate the infrared light source at a first wavelength, illuminate the infrared light source at a second wavelength, illuminate the infrared light source at a third wavelength, capture an image, and generate a color image of a fundus of a patient's eye based on a lightness map.

The details of one or more embodiments are set forth in the accompanying drawings and the description below. Other features, objects, and advantages of these embodiments will be apparent from the description, drawings, and claims.

DESCRIPTION OF THE DRAWINGS

The following drawing figures, which form a part of this application, are illustrative of described technology and are not meant to limit the scope of the disclosure as claimed in any manner, which scope shall be based on the claims appended hereto.

DETAILED DESCRIPTION

The present disclosure is directed to systems and methods for non-mydriatic infrared color eye fundus imaging. Non-mydriatic imaging involves a patient who has not been administered a pharmacological pupil dilation substance. Thus, the patient's eyes are not artificially dilated. The sensation of artificially dilated pupils can be uncomfortable or even painful for some patients. Moreover, most pharmacological pupil dilation substances do not act instantaneously.

Pupil dilation is somewhat inversely related to the amount of ambient light. However, low lighting conditions can affect image quality. One solution is to briefly flash a light during capturing an image of a patient's eye fundus. But a bright flash in a dimly-lit room can be uncomfortable and jarring for patients. Such light can also reduce pupil dilation.

Near-infrared light can be used as an illumination source in a low-light environment without patient discomfort because near-infrared light is undetectable by the human eye. However, infrared light can be detected by image sensor arrays. Images produced using solely infrared light are typically monochrome.

As used herein, "infrared" means near-infrared, from about 700 nm to about 2500 nm, unless otherwise noted.

Figure 1:
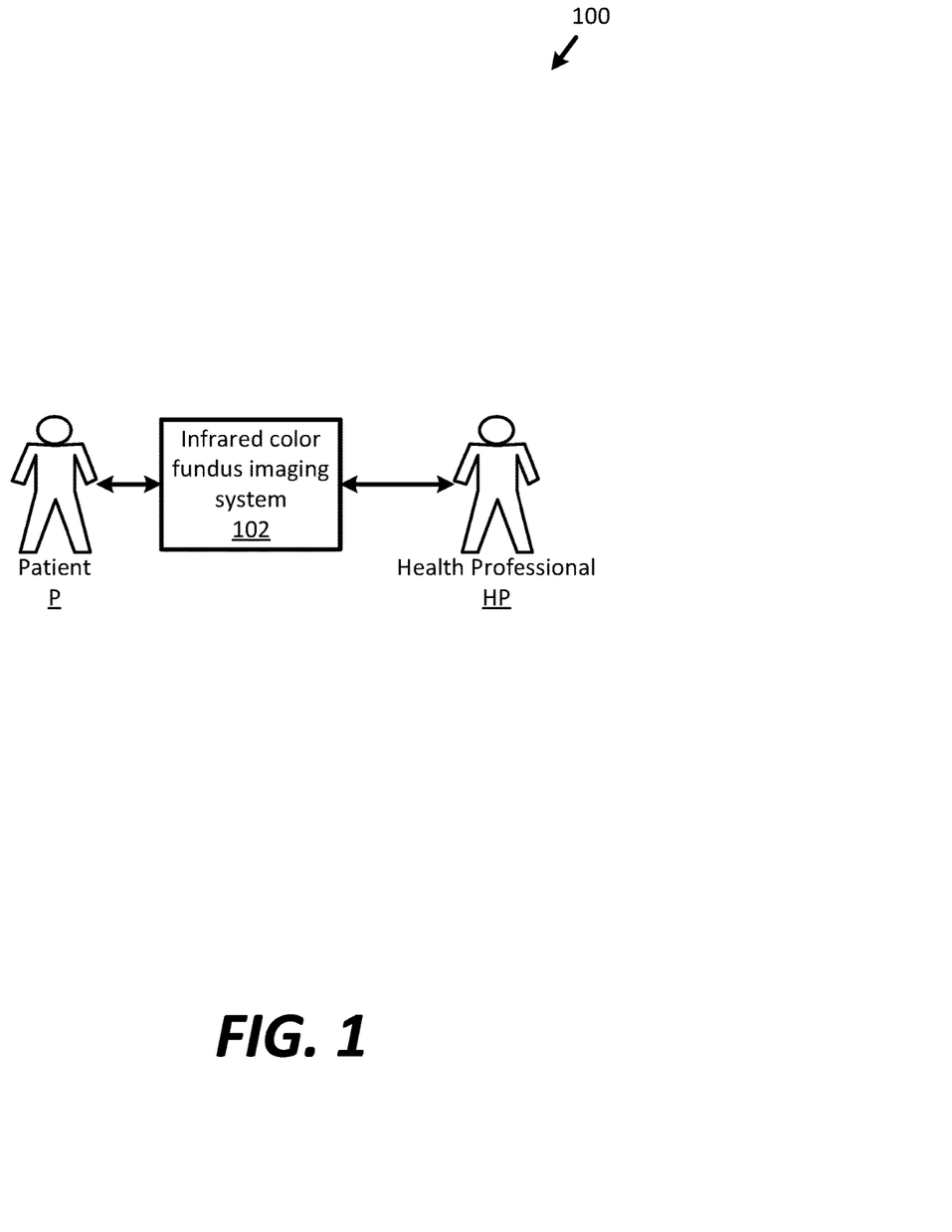
FIG. 1 illustrates an example environment for an infrared fundus imaging system.

FIG. 1 illustrates an embodiment of an example fundus imaging system 100. The example fundus imaging system 100 includes a patient P, a health professional HP, and an infrared fundus imaging system 102. The health professional HP operates the infrared fundus imaging system 102 to view images of the patient's P eye fundus. The infrared fundus imaging system 102 is typically used in a clinical environment. In embodiments, the infrared fundus imaging system 102 is used in a non-healthcare location. Other embodiments can include more or fewer people and components.

The infrared fundus imaging system 102 generates color, digital images of a patient's P eye fundus. As used herein, "fundus" refers to the eye fundus and includes the retina, optic nerve, macula, vitreous, choroid and posterior pole.

In embodiments, the health professional HP uses the infrared fundus imaging system 102 to screen for, diagnose, or monitor the patient P for an eye disease, diabetic retinopathy. The infrared fundus imaging system 102 can be used to screen for, monitor, or diagnose various other eye diseases.

The health professional HP operating the infrared fundus imaging system 102 may be different from the health professional HP that evaluates the fundus images. For example, a nurse operates the infrared fundus imaging system 102 and a physician views and evaluates the generated color fundus images.

Most known techniques for fundus imaging require mydriasis, which is the dilation of the patient's pupil. Example fundus imaging system 100 does not require a mydriatic drug to be administered to the patient P before imaging. However, the fundus imaging system 100 can be used if a mydriatic drug was administered to the patient P.

Figure 2:
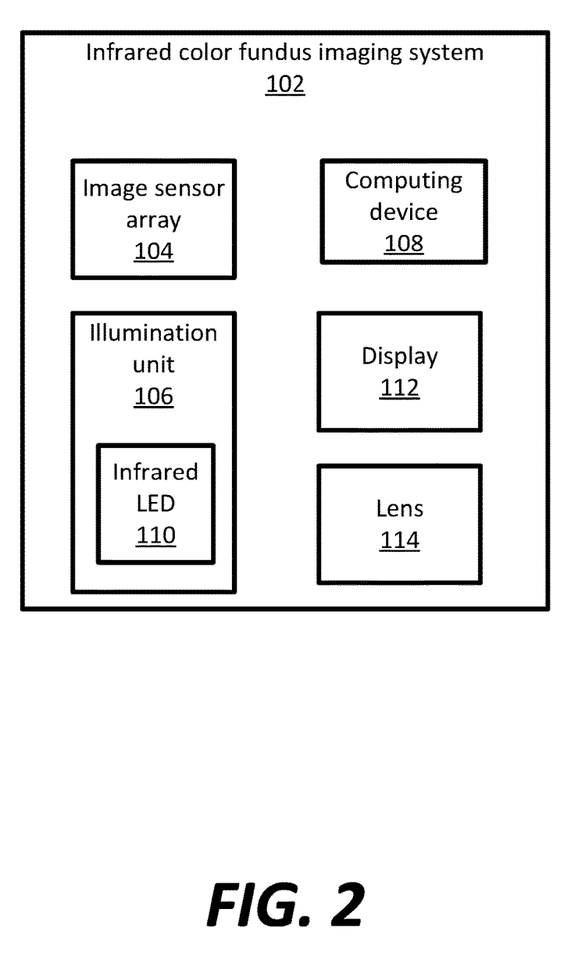
FIG. 2 illustrates a block diagram of components included in an embodiment of an example infrared fundus imaging system.

FIG. 2 is a block diagram of the components in an embodiment of the example infrared fundus imaging system 102. The example infrared fundus imaging system 102 includes an image sensor array 104, an illumination unit 106 with an infrared LED 110, a computing device 108, a display 112, and a lens 114. A housing supports the components of infrared fundus imaging system 102. Computing device 108 is in communication with all electrical components of infrared fundus imaging system 102. Other embodiments can include more or fewer components.

Image sensor array 104 receives light reflected by the patient's P fundus. Image sensor array 104 is either a complementary metal-oxide semiconductor (CMOS) or charge-coupled device (CCD) sensor array. In both the CMOS and CCD embodiments, image sensor array 104 is a monochrome sensor. The monochrome sensor includes monochrome photodiodes with light-receiving surfaces and that have substantially uniform length and width.

Exposure of image sensor array 104 can be controlled as a global shutter. That is, substantially all of the photodiodes in image sensor array 104 are exposed simultaneously and for substantially identical lengths of time. The global exposure effectively integrates charge substantially evenly across the image sensor array 104 during the exposure time.

Image sensor array 104 captures digital images and processing of those images can be done in various formats, such as RAW, JPEG, BITMAP, TIFF, etc.

Many commercial image sensor arrays come with a hot mirror filter and/or a color filter array. Hot mirror filters effectively block infrared light from reaching the image sensor array but allow visible light to pass through and reach the image sensor array. Color filter arrays are positioned over the pixel sensors in an image sensor array and include an arrangement of colors, such as red, green, and blue filters. These filters filter the incident light by wavelength.

Because the patient's P fundus is illuminated using infrared light, however, a hot mirror filter and/or a color filter array would block most or all of the infrared light reflected by the patient's P eye fundus. Thus, example image sensor array 104 does not include a hot mirror filter and does not include a color filter array that blocks infrared light.

In embodiments, image sensor array 104 includes a cold mirror filter. Cold mirror filters reflect visible light but allow infrared light to pass through. Alternatively, an infrared filter can be mounted over the lens 114 that blocks all but the infrared light.

In other embodiments, the example image sensor array 104 does not include any filter, which can enhance the imaging quality without signal loss as compared to embodiments using some type of optical filter. The relatively improved image quality can be attributed, at least in part, to the fact that the fundus camera is usually operated in a dimly-lit environment.

Illumination unit 106 includes one or more infrared light sources that illuminate the patient's P eye fundus. The infrared light source can include one or more infrared light-emitting diodes (LEDs) 110. Illumination unit 106 includes three LEDs that emit light at wavelengths of 760 nanometers (nm), 850 nm, and 950 nm. Different wavelengths are used in other embodiments, such as, for example, 770 nm, 810 nm, 870 nm, 880 nm, and 940 nm.

In embodiments where more than one infrared LED 110 is used in illumination unit 106, the wavelengths of the LEDs are selected such that the wavelengths differ by at least about 20 nm, about 30 nm, about 40 nm, about 50 nm, about 60 nm, about 70 nm, about 80 nm, about 90 nm, or about 100 nm. The differences in wavelengths between the three infrared LEDs 110 can be equal or non-equal. For example, in the embodiment above the differences are non-equal: the difference between the first two wavelengths is 90 nm, and the difference between the second and the third wavelengths is 100 nm.

Computing device 108 causes illumination unit 106 to illuminate the infrared LEDs 110 in combination with the image sensor array 104 capturing images of the patient's P fundus. For example, three images are captured by image sensor array 104 during three separate illuminations of the three infrared LEDs 110. Alternatively, or in addition, all three infrared LEDs 110 are illuminated substantially simultaneously and the image sensor array 104 captures one or more images during the combined illumination of the patient's P fundus. Alternatively, or in addition, an first image is captured by the image sensor array 104 while one infrared LED 110 is illuminated, a second image is captured by the image sensor array 104 while two infrared LEDs 110 are illuminated, and a third image is captured by the image sensor array 104 while three infrared LEDs are illuminated.

Figure 6:
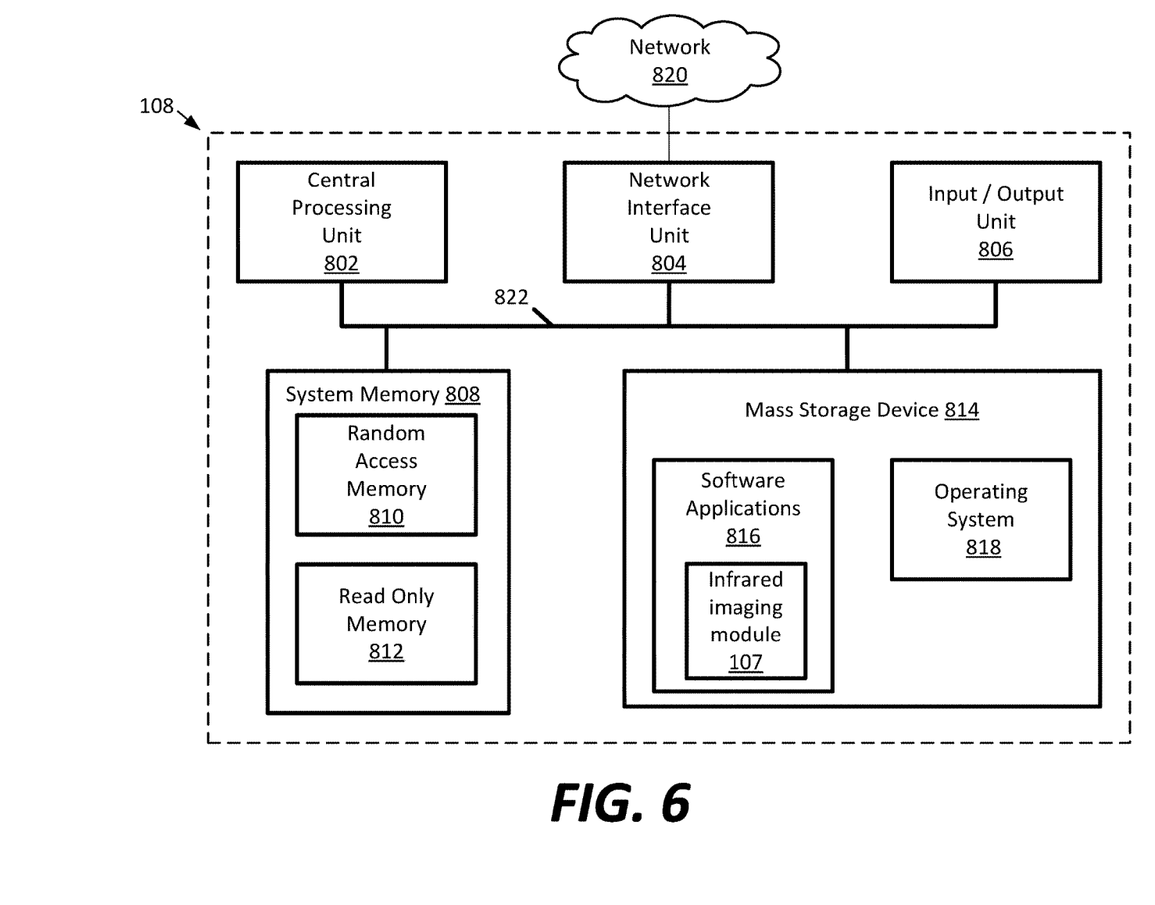
FIG. 6 illustrates an example computing unit used in the example infrared fundus imaging system.

As mentioned above, computing device 108 is in communication with, at least, image sensor array 104, illumination unit 106, and display 112. Computing device 108 includes mass storage device 814 that includes infrared imaging module 107, shown in FIG. 6. Infrared imaging module 107 includes instructions that, when executed by a central processing unit 802 (a processor), control the illumination unit 106 and image sensor array 104 during fundus image capture. Example components of computing device 108 are shown in FIG. 6 and described in more detail below.

Display 112 provides a graphical user interface that guides the healthcare professional HP during evaluation and displays the fundus images. Display 112 is, for example, a liquid crystal display (LCD) or active matrix organic light emitting display (AMOLED) supported by the housing of infrared fundus imaging system. Display 112 can show a live view from image sensor array 104, possibly in combination with on-screen directions, to aid the healthcare professional HP in positioning and/or focusing the infrared fundus imaging system.

In embodiments, computing device 108 is in communication with an external display, such as a computer monitor, and transmits the fundus images to the external display for evaluation by the healthcare professional HP. Transmission of the fundus images from computing device 108 to external display can be via wired or wireless connections.

The example infrared fundus imaging system 102 also includes a lens 114 supported by the housing. Some embodiments have more than one lens supported by the housing. For example, one lens is used to focus the light incident on the image sensor array 104, and another lens is used to focus the light from the illumination unit 106. Some embodiments use more than one lens to focus the incident light.

In embodiments, the lens has mechanical power and control connections coupled to the computing device 108. The computing device 108 may be configured to control the position of the lens or lenses to optimize lens positioning for auto focusing for the image sensor array 104 and illumination unit 106. In some embodiments, unique facial geometries require lens focusing even where there is a standard positioning guide adjacent to, or integral with, infrared fundus imaging system.

Infrared fundus imaging system 102 can also include reflective mirrors, not shown in FIG. 2. The optional one or more reflective mirrors are used to direct light to the image sensor array 104 and from illumination unit 106. The mirrors are supported by the housing and, in embodiments, can be adjusted and/or pivoted by computing device 108.

Figure 3:
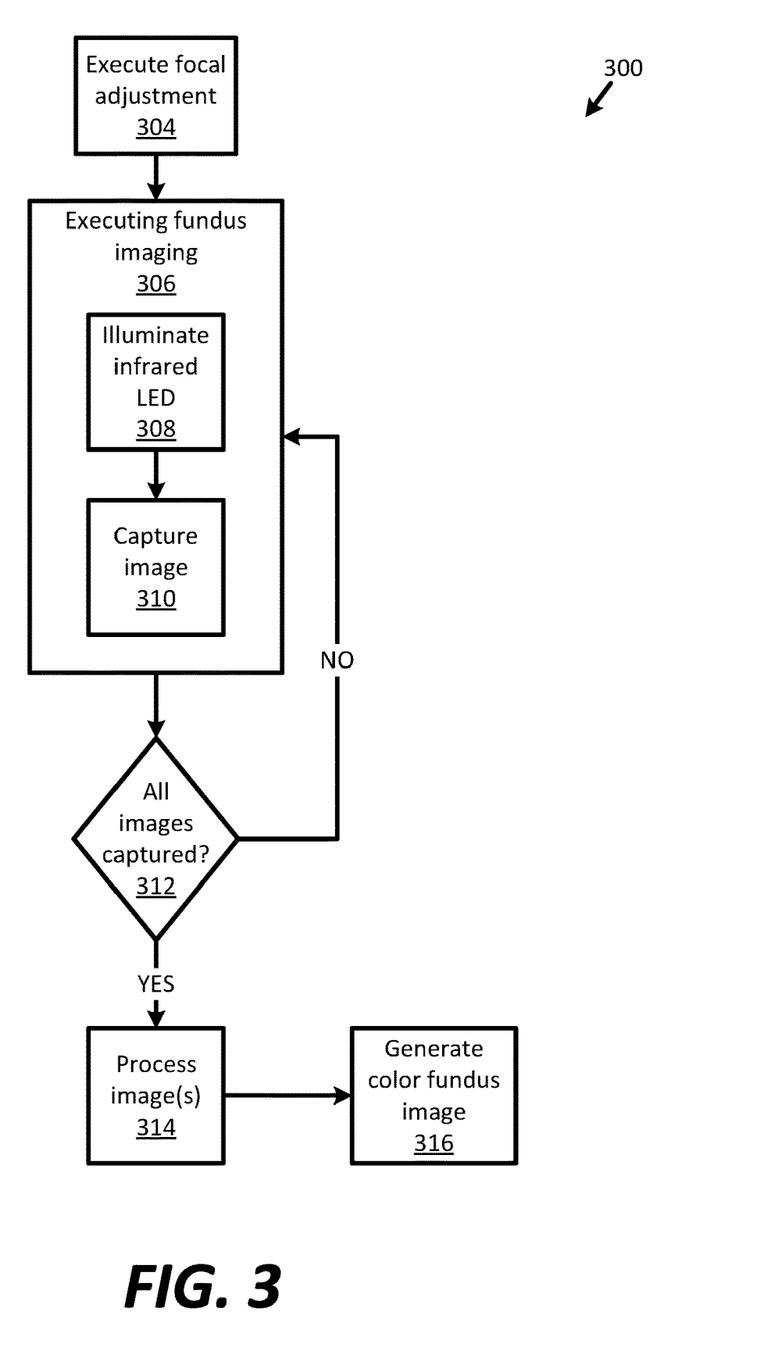
FIG. 3 illustrates an example method for generating a color fundus image.

FIG. 3 illustrates an embodiment of an example method 300 for generating a color fundus image using the infrared fundus imaging system 102. The example method 300 includes executing a focal adjustment (operation 304), executing fundus imaging (operation 306), which includes illuminating one or more infrared LEDs (operation 308) and capturing an image (operation 310), determining whether all images have been captured (operation 312), processing the images (operation 314), and generating a color fundus image (operation 316). A healthcare professional HP initiates example method 300 in a dimly-lit environment. Other embodiments can include more or fewer operations.

The example method 300 begins with a focal adjustment (operation 304). At this point, patient P is positioned, either seated or standing. Positioning includes aligning the patient P such that one or more of the patient's P eyes are aligned with the aperture of the infrared fundus imaging system 102. In embodiments, display 112 provides a preview image to help guide the healthcare professional HP in positioning the patient P.

In embodiments, a positioning structure, such as a chin rest or head support structure, assists in positioning the patient P. The positioning structure can be adjusted by the healthcare professional HP to maneuver the patient P relative to the housing of the infrared fundus imaging system 102. The housing additionally can be adjustable relative to the patient P.

Focal adjustment (operation 304) can be done mechanically by the healthcare professional HP and/or automatically by computing device 108 using auto-focusing algorithms. In embodiments, infrared fundus imaging system 102 has one or more adjustable foci. The focus adjusts the position of the lens 114 through which the incident light passes. In embodiments, the focus also adjusts the lens through which the light from the illumination unit passes. The healthcare professional HP can initiate automatic focusing by pressing a button on the housing or selecting an icon on display 112. In embodiments, one or more infrared LEDs are illuminated during the focal adjustment (operation 304).

After the focus is adjusted (operation 304), the infrared fundus imaging system 102 executes fundus imaging (operation 306), which includes illuminating one or more infrared LEDs (operation 308) and capturing an image (operation 310).

While the infrared LED is illuminated (operation 308), the infrared fundus imaging system 102 captures an image of the patient's P fundus (operation 310). As discussed above, one, two or three infrared LEDs are illuminated at a given time, depending upon the embodiment. Computing device 108 records the wavelength of the infrared LED illuminated and tags the captured image or associates the captured image with the wavelength data, which can be used during image processing (operation 314).

Where two or more images are captured with different near-infrared illumination wavelengths, the two or more images are captured in quick succession. For example, three images are captured within 10 ms. Then, when the images are later combined to produce a color image, there is less likelihood that the pixels among the three images do not correspond to each other.

Figure 5:
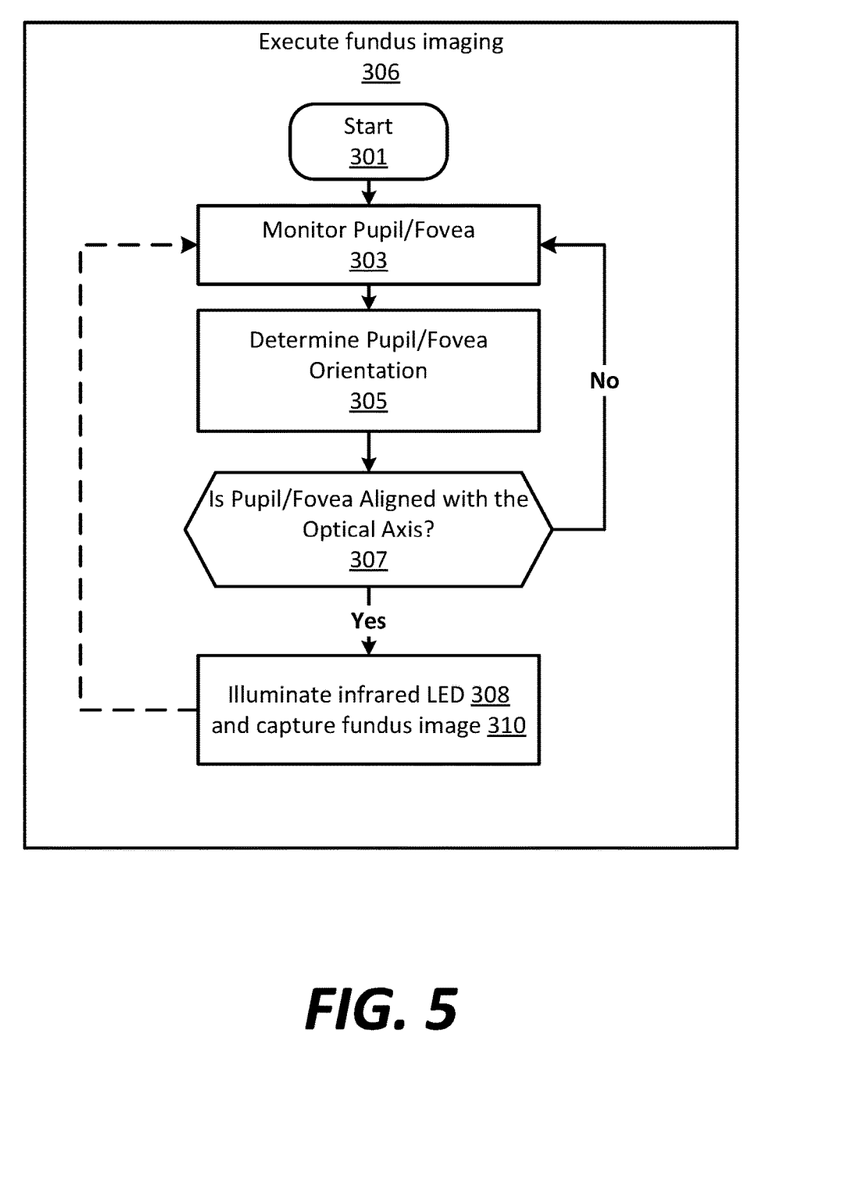
FIG. 5 illustrates an example method for initiating image capture using passive eye tracking.

In embodiments, executing fundus imaging (operation 306) is initialized using passive eye tracking, and embodiment of which is shown in FIG. 5. Referring now to FIG. 5, execute fundus imaging (operation 306) proceeds to illuminate infrared LEDs (operation 308) and capture image (operation 310) by monitoring the pupil/fovea orientation of the patient P.

First, the pupil, fovea, or both of the patient P is monitored (operation 303). Infrared fundus imaging system 102 captures images in a first image capture mode. In the first image capture mode, the infrared fundus imaging system 102 captures images at a higher frame rate. In embodiments, the first image capture mode is conducted at lower resolutions.

Next, the computing device 108 processes at least a portion of the captured images (operation 305). The computing device 108 processes the images to identify the location of the pupil or fovea or both of the patient P. Using the location of the pupil or fovea or both in one of the images, a vector corresponding to the pupil/fovea orientation is calculated. In embodiments, the pupil/fovea orientation is approximated based on the distance between the pupil and fovea in the image. In other embodiments, the pupil/fovea orientation is calculated by approximating the position of the fovea relative to the pupil in three dimensions using estimates of the distance to the pupil and the distance between the pupil and the fovea. In other embodiments, the pupil/fovea orientation is approximated from the position of the pupil alone. Still other methods of approximating the pupil/fovea orientation are possible.

Then the pupil/fovea orientation is compared to an optical axis of the infrared fundus imaging system 102 (operation 307). If the pupil/fovea orientation is substantially aligned with the optical axis of the infrared fundus imaging system 102, then the process proceeds to illuminate infrared LED (operation 308) and capture fundus image (operation 310). If not, the process returns to continue to monitor the pupil or fovea (operation 303). In embodiments, the pupil/fovea orientation is substantially aligned with the optical axis when the angle between them is less than two to fifteen degrees.

In embodiments, execute fundus imaging (operation 306) returns to monitor the pupil/fovea orientation (operation 303). Further information regarding passive eye tracking can be found in U.S. patent application Ser. No. 14/177,594, titled Ophthalmoscope Device, which is hereby incorporated by reference in its entirety.

Returning now to FIG. 3, after capturing an image (operation 310), the infrared fundus imaging system 102 checks whether all images have been captured (operation 312). In embodiments, the color fundus image is generated from three images captured when three different infrared LEDs were illuminated. In those embodiments, then, the system at operation 312 evaluates whether three images at three different wavelengths have been captured. If all images have not been captured, then method 300 returns to execute fundus imaging (operation 306). Otherwise, method 300 proceeds to process images (operation 314) and the healthcare professional HP can be notified via display 112 that all required images have been captured.

Operation 312 optionally includes an image focus analysis of the image. If the captured image is not properly focused, method 300 can return to execute focal adjustment (operation 304) and capture additional images until acceptable images are captured.

If the images have all been captured, then the infrared fundus imaging system 102 proceeds to process the images (operation 314). Infrared fundus imaging system 102 processes the RAW data files or a compressed image file, such as TIFF, JPEG, BITMAP, etc. Processing images (operation 314) is shown and described below in more detail with reference to FIG. 4.

One output of processing images (operation 314) is that one or more color fundus images are generated (operation 316). These color fundus images can be shown to a healthcare provider HP on display 112 or on an external display. Should the healthcare provider HP desire to view the images in black and white, monochrome images can also be generated by infrared fundus imaging system 102 and displayed to the healthcare provider HP.

Figure 4:
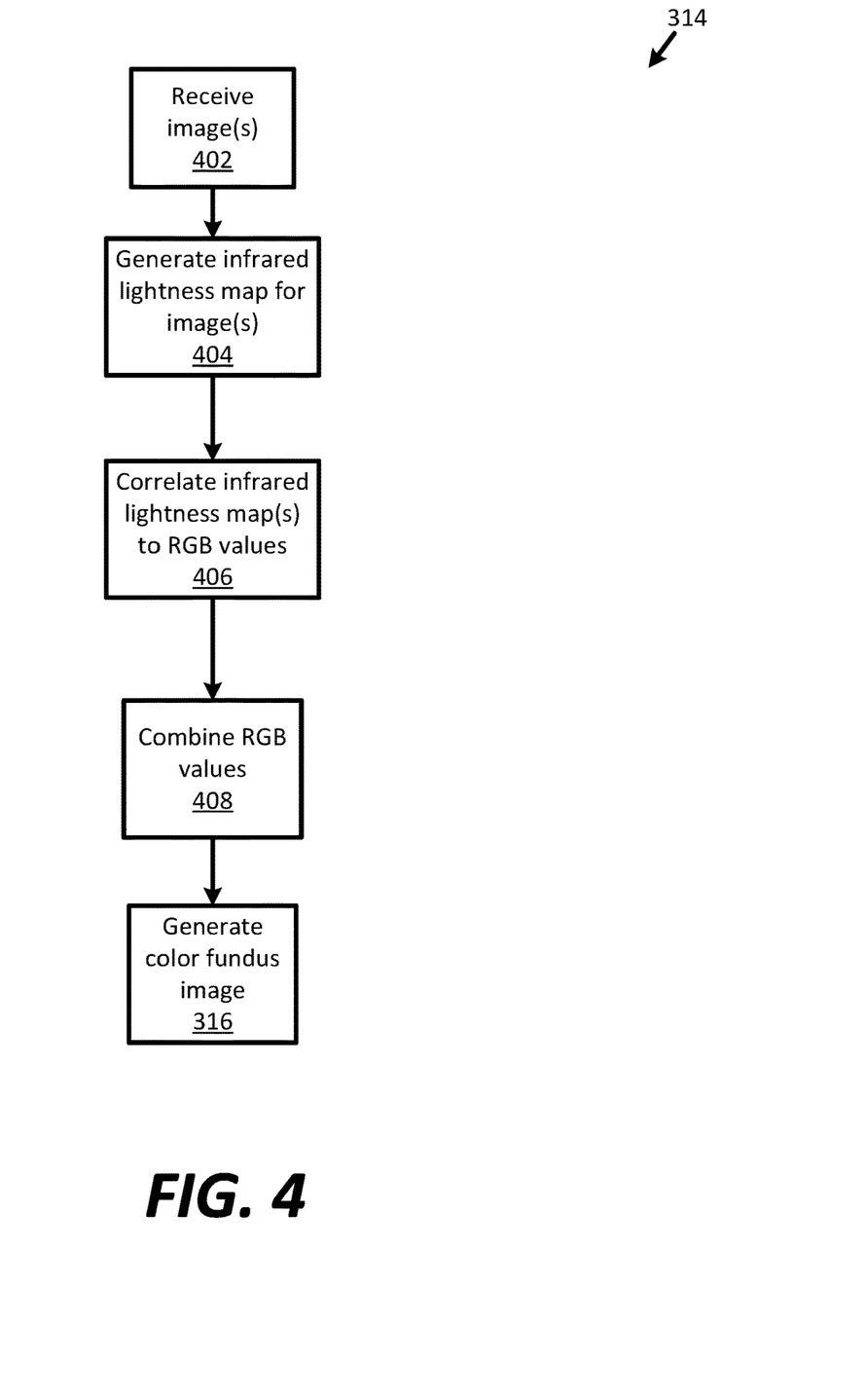
FIG. 4 illustrates an example method for image processing.

FIG. 4 illustrates an embodiment of example image processing (operation 314). The example image processing includes receiving one or more images (operation 402), generating an infrared lightness map for each image (operation 404), correlating the one or more generated infrared lightness maps to red, green and blue (RGB) values (operation 406), combining the RGB values (operation 408), and generating a color fundus image (operation 316). Other embodiments can include more or fewer operations.

The example image processing begins by receiving one or more images (operation 402). The images are digital files, such as RAW data files or a compressed image file, such as TIFF, JPEG, BITMAP, etc. The images, or data associated with the images received in operation 402, can also include data about the lighting conditions when the images were captured.

Next, an infrared lightness map is generated each received image (operation 404). In embodiments, the infrared lightness map is generated by determining the radiance of each pixel at a given wavelength. For example, take an image captured when a 760 nm LED was illuminated. Each pixel on the image sensor array recorded a value and the lightness map is a value corresponding to the radiance of the recorded value. Each of those values corresponds to 760 nm. This operation can be repeated for every pixel in every image received.

Then the infrared lightness map for each received image is correlated to red-green-blue values (operation 406). Theoretically, there is a relationship between the detected radiance and the actual color present in the patient's P eye fundus. That relationship can be nonlinear depending upon the given wavelength. Here, a delta value (Δ) is determined between the lightness map and the corresponding RGB value. The delta value can also include a magnitude determination.

After correlating the lightness map to RGB values (operation 406), the RGB values are combined (operation 408). In embodiments where three images are captured at three different near-infrared illumination wavelengths, the delta values for each of the three images are combined to determine what color is actually present at that pixel, based on the radiance and magnitude of radiance at the different near-infrared wavelengths. The combined RGB values are then used to generate one or more color fundus images (operation 316).

FIG. 6 shows an embodiment of an example computing device 108 hosting the infrared imaging module 107. As illustrated, the example computing device 108 includes at least one central processing unit ("CPU") 802, a system memory 808, and a system bus 822 that couples the system memory 808 to the CPU 802. The system memory 808 includes a random access memory ("RAM") 810 and a read-only memory ("ROM") 812. A basic input/output system that contains the basic routines that help to transfer information between elements within the example computing device 108, such as during startup, is stored in the ROM 812. The example computing device 108 further includes a mass storage device 814. The mass storage device 814 is able to store software instructions and data.

The mass storage device 814 is connected to the CPU 802 through a mass storage controller (not shown) connected to the system bus 822. The mass storage device 814 and its associated computer-readable data storage media provide non-volatile, non-transitory storage for the example computing device 108. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 108.

According to various embodiments of the inventions, the example computing device 108 may operate in a networked environment using logical connections to remote network devices through the network 820, such as a wireless network, the Internet, or another type of network. The example computing device 108 may connect to the network 820 through a network interface unit 804 connected to the system bus 822. It should be appreciated that the network interface unit 804 may also be utilized to connect to other types of networks and remote computing systems. The example computing device 108 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 108 can store software instructions and data. The software instructions include an operating system 818 suitable for controlling the operation of the example computing device 108. The mass storage device 814 and/or the RAM 810 also store software instructions, that when executed by the CPU 802, cause the example computing device 108 to provide the functionality of the example computing device 108 discussed in this document. For example, the mass storage device 814 and/or the RAM 810 can store software instructions that, when executed by the CPU 802, cause the example computing device 108 to display received data on the display screen of the example computing device 108.

The description and illustration of one or more embodiments provided in this application are not intended to limit or restrict the scope of the inventions as claimed in any way. The embodiments, examples, and details provided in this application are considered sufficient to convey possession and enable others to make and use the best mode of claimed inventions. The claimed inventions should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed inventions and the general inventive concept embodied in this application that do not depart from the broader scope.

The invention claimed is:

1. A non-mydriatic fundus imaging apparatus, comprising:
    a processor and a memory;
    an infrared light source operatively coupled to the processor; and an image sensor array operatively coupled to the processor,
wherein the memory stores instructions that, when executed by the processor, cause the non-mydriatic fundus imaging apparatus to:
illuminate the infrared light source at a first wavelength;
illuminate the infrared light source at a second wavelength;
illuminate the infrared light source at a third wavelength;
wherein each of the first wavelength, the second wavelength, and the third wavelength is different;
capture a first image during illumination of the infrared light source at the first wavelength;
capture a second image during illumination of the infrared light source at the second wavelength;
capture a third image during illumination of the infrared light source at the third wavelength; and
generate a color image of a fundus of a patient's eye based on a lightness map for each of the first image, the second image, and the third image, each lightness map including a radiance level of a plurality of pixels, the color image being generated by:
correlate each lightness map to red, green, and blue (RGB) values; and
generate the color image of the fundus by combining the RGB values.

2. The apparatus of claim 1, wherein the memory further stores instructions that, when executed by the processor, cause the apparatus to:
generate a first lightness map for the first image, the first lightness map including a radiance level of a plurality of pixels of the first image,
generate a second lightness map for the second image, the second lightness map including a radiance level of a plurality of pixels of the second image, and
generate a third lightness map for the third image, the third lightness map including a radiance level of a plurality of pixels of the third image.

3. The apparatus of claim 1, wherein the image sensor array is a global shutter.

4. The apparatus according to claim 1, wherein the infrared light source includes a first light-emitting diode at the first wavelength, a second light-emitting diode at the second wavelength, and a third light-emitting diode at the third wavelength.

5. The apparatus according to claim 4, wherein a difference between the first wavelength and the second wavelength is at least 50 nm, wherein a difference between the second wavelength and the third wavelength is at least about 50 nm, and wherein a difference between the first wavelength and the third wavelength is at least about 100 nm.

6. The apparatus according to claim 4, wherein a wavelength of the first light-emitting diode is 760 nm.

7. The apparatus according to claim 4, wherein a wavelength of the second light-emitting diode is 850 nm.

8. The apparatus according to claim 4, wherein a wavelength of the third light-emitting diode is 950 nm.

9. The apparatus of claim 4, wherein the memory further stores instructions that, when executed by the processor, cause the non-mydriatic fundus imaging apparatus to:
illuminate simultaneously each of the first light-emitting diode, the second light-emitting diode, and the third light-emitting diode.

10. The apparatus of claim 1, wherein the image sensor array is configured to receive infrared light.

11. The apparatus of claim 10, wherein the image sensor array includes an infrared filter.

12. The apparatus of claim 10, wherein the image sensor array includes a cold mirror filter.

13. A method of non-mydriatic fundus imaging, the method comprising:
illuminating an infrared light source at a first wavelength;
illuminating the infrared light source at a second wavelength;
illuminating the infrared light source at a third wavelength;
wherein each of the first wavelength, the second wavelength, and the third wavelength is different;
capturing a first image at the first wavelength, a second image, at the second wavelength, and a third image at the third wavelength;
generating an infrared lightness map for each of the first image, the second image, and the third image, with each infrared lightness map including a radiance level of a plurality of pixels; and
generating a color image of a fundus of a patient's eye based on each infrared lightness map, including:
correlating each infrared lightness map to red, green, and blue (RGB) values;
determining a delta value for each of the first image, the second image, and the third image; and
generating the color image of the fundus by combining the RGB values using the delta value.

14. The method according to claim 13, further comprising:
capturing a first image while illuminating the infrared light source at the first wavelength;
capturing a second image while illuminating the infrared light source at the second wavelength;
capturing a third image while illuminating the infrared light source at the third wavelength; and
wherein generating each infrared lightness map includes:
generating a first lightness map for the first image,
generating a second lightness map for the second image, and
generating a third lightness map for the third image.

15. The method according to claim 13, further comprising:
adjusting a focal length prior to capturing the image of the fundus.

16. A non-mydriatic fundus imaging system, comprising:
a processor and a memory;
an infrared light source operatively coupled to the processor; and
an image sensor array operatively coupled to the processor,
wherein the memory stores instructions that, when executed by the processor, cause the non-mydriatic fundus imaging system to:
illuminate the infrared light source at a first wavelength, a second wavelength, and a third wavelength;
capture a first image when the infrared light source is illuminated at the first wavelength;
capture a second image when the infrared light source is illuminated at the second wavelength;
capture a third image when the infrared light source is illuminated at the third wavelength;
wherein each of the first wavelength, the second wavelength, and the third wavelength is different;
generate an infrared lightness map for each of the first image, the second image, and the third image, each infrared lightness map including a radiance level of a plurality of pixels of the first image, the second image, and the third image;
based on each infrared lightness map, generate a color fundus image, including:
correlate each infrared lightness map to red, green, and blue (RGB) values;
determine a delta value for each of the first image, the second image, and the third image; and
generate the color image of the fundus by combining the RGB values using the delta value.

* * * * *